United States Patent
Neethling

(10) Patent No.: US 10,758,642 B2
(45) Date of Patent: Sep. 1, 2020

(54) STERILIZATION PROCESS

(71) Applicant: Admedus Regen Pty Ltd, Malaga (AU)

(72) Inventor: William Morris Leonard Neethling, Booragoon (AU)

(73) Assignee: Admedus Regen Pty Ltd., Malaga (AU)

( * ) Notice: Subject to any disclaimer, the term of this patent is extended or adjusted under 35 U.S.C. 154(b) by 0 days.

(21) Appl. No.: 15/150,025

(22) Filed: May 9, 2016

(65) Prior Publication Data

US 2016/0287748 A1 Oct. 6, 2016

Related U.S. Application Data

(63) Continuation of application No. 13/561,787, filed on Jul. 30, 2012, now abandoned.

(30) Foreign Application Priority Data

Nov. 10, 2011 (AU) ................................ 2011904681

(51) Int. Cl.

| | |
|---|---|
| *A61L 27/24* | (2006.01) |
| *A61L 27/36* | (2006.01) |
| *A61L 2/00* | (2006.01) |
| *A61L 2/16* | (2006.01) |
| *A61K 41/10* | (2020.01) |

(52) U.S. Cl.
CPC .............. *A61L 27/24* (2013.01); *A61K 41/10* (2020.01); *A61L 2/0088* (2013.01); *A61L 27/3604* (2013.01); *A61L 27/3687* (2013.01); *A61L 2202/21* (2013.01); *A61L 2400/02* (2013.01); *A61L 2430/20* (2013.01)

(58) Field of Classification Search
CPC ...................................................... A61K 41/10
See application file for complete search history.

(56) References Cited

U.S. PATENT DOCUMENTS

| | | | | |
|---|---|---|---|---|
| 2,817,437 | A | * 12/1957 | George | ............ A61B 17/06128 206/63.3 |
| 5,503,638 | A | 4/1996 | Cooper et al. | |
| 5,782,914 | A | 7/1998 | Schankereli | |
| 2003/0068815 | A1 | 4/2003 | Stone et al. | |
| 2011/0263927 | A1 | 10/2011 | Gellman et al. | |
| 2013/0122583 | A1 | 5/2013 | Neethling | |

FOREIGN PATENT DOCUMENTS

| | | |
|---|---|---|
| JP | 61-90673 A | 5/1986 |
| JP | 2006-511246 A | 4/2006 |
| WO | WO 03/097809 A2 | 11/2003 |

OTHER PUBLICATIONS 12847101.8, European Search Report.
CN 2012800665748, Translation of Chinese Office Action.
European Search Report for EP Application No. 12847101.8 dated Jun. 8, 2015.
Translation of Chinese Office Action issued in connection with CN2012800665748.
Anson et al., Bovine pericardium for dural grafts: clinical results in 35 patients. Neurosurgery. Oct. 1996;39(4):764-8.
Chv Apil et al., Effect of collagen crosslinking on the rate of resorption of implanted collagen tubing in rabbits. J Biomed Mater Res. Mar. 1977;11(2):297-314.
Database WPI; Thomson Scientific, London, GB; AN 1986-158631 & JP 61 090673 A (Agency of Ind. Sci. & Technology) May 8, 1986.
McDonnell et al., Antiseptics and disinfectants: activity, action, and resistance. Clin Microbiol Rev. Jan. 1999;12(1):147-79.
Neethling et al., Enhanced biostability and biocompatibility of decellularized bovine pericardium, crosslinked with an ultra-low concentration monomeric aldehyde and treated with ADAPT. J Heart Valve Dis. Jul. 2008;17(4):456-63; discussion 464.
Sung, Hsing-Wen, et al; "Effects of various chemical sterilization methods on the crosslinking and enzymatic degradation characteristics of an epoxy-fixed biological tissue"; Journal of Biomedical Material Research, Dec. 5, 1997, pp. 376-383.
Wright, The sterilizing capactiy of propylene oxide and chlorhexidine diacetate solutions upon pre-injection swabs saturated with propan-2-ol. J Hyg (Lond). Oct. 1983;91(2):287-92.
U.S. Appl. No. 13/561,787, filed Jul. 30, 2012, Neethling.
PCT/AU2012/001388, Jan. 29, 2013, International Search Report.
International Search Report dated Jan. 29, 2013 for Application No. PCT/AU2012/001388.
Avery & Bailey (2008), In: Collagen: Structure and Mechanics: Ed P Fratzl, Chapter 4, p. 104, Springer Science & Business Media—extract of p. 104 attached.
Hart et al., Propylene oxide as sterilizing agent. Appl Microbiol. Dec. 1974;28(6):1069-70.
Nimni, Chapter 3: Collagen in Cardiovascular Tissues. In: Cardiovascular Biomaterials: Ed: GW Hastings. Springer-Verlag, London. 1992. p. 81.

* cited by examiner

*Primary Examiner* — Marsha Tsay
(74) *Attorney, Agent, or Firm* — N.V. Nederlandsch Octrooibureau; Catherine A. Shultz; Katelyn J. Bernier

(57) ABSTRACT

The present invention relates to a process for sterilizing implantable biomaterials. In particular, the invention relates to a process for sterilizing collagen-containing implantable biomaterials and storage thereafter.

18 Claims, 2 Drawing Sheets

STERILIZATION PROCESS

CROSS REFERENCE TO RELATED APPLICATION

This application is a continuation application of U.S. application Ser. No. 13/561,787, filed Jul. 30, 2012, which claims the benefit of Australian Patent Application No. 2011904681, filed Nov. 10, 2011, the entire contents of the aforementioned applications are hereby incorporated herein by reference.

FIELD

The present invention relates to a process for sterilizing implantable biomaterials. In particular, the invention relates to a process for sterilizing collagen-containing implantable biomaterials and storage thereafter.

BACKGROUND

Implantable biomaterials, especially collagen-based biomaterials, require sterilization and most often storage before use. Generally there are two broad classes of implantable collagen-based biomaterials: (1) natural tissue and (2) chemically cross-linked tissue. Thus, depending upon the type of collagen-based biomaterial and whether or not cross-linking has taken place there is a need for a means of sterilizing the tissue as well as storing tissue once it has been sterilized.

Chemical cross-linked collagen-based biomaterials such as cardiovascular patches, heart valves, matrices and arteries are usually sterilized after cross-linking and stored in a sterile solution until implantation. Several sterilization methods for chemical cross-linked collagen-based biomaterials have been tested and implemented over the past three to four decades including gamma irradiation, UV irradiation and a variety of chemical agents. Although most of these sterilization methods are efficient in preventing contamination, adverse effects such as structural damage (cleaving of peptide bonds) and tissue degeneration (reduction in tensile strength) has made a number of these methods less appealing for industrial application.

For example, collagen-based biomaterials cross-linked with glutaraldehyde can become chemically unstable when exposed to alcohol-based sterilisation solutions due to the interaction of the alcohol with residual and unbound glutaraldehyde present in the tissue. Unstable hemiacetyls are formed when an alcohol reacts with an aldehyde. These unstable hemiacetyls have the capacity to react with alcohol to form an acetyl, which can dissociate to form an aldehyde and an alcohol.

Thus, at present, the majority of manufacturers of collagen-based biomaterials prefer the use of glutaraldehyde-formaldehyde combinations for chemical cross-linking and non-aldehyde agents for sterilization. One such non-aldehyde agent is ethylene oxide (oxirane) gas, which has been used to sterilize mechanical heart valves for many years. Ethylene oxide gas has also been used to sterilize a variety of medical equipment, disposable items and mechanical heart valves.

Once the collagen-based biomaterial has been sterilized it is generally stored for a period of time before implantation. Mid- to long-term storage of collagen-based biomaterials requires adequate protection from contamination in a physiologically stable solution. Although most of the commercially available collagen-based biomaterials are still stored in aldehyde-based solutions, adverse effects such as calcification and fibrosis are well known.

Since the 1970's propylene oxide has been used as a sterilizing agent (see, for example, Hart & Brown, 1974, *Appl Microbiol,* December p.1069-1070; Brown & Ng, 1975, *Appl Microbiol,* September p483-484). In each case a solution comprising 5% propylene oxide plus 70% isopropyl alcohol or 0.5% chlorhexidine or 2% Cetrimide was effective in destroying a bacterial spore suspension. However, while the use of propylene oxide has been recorded this is usually applied in the presence of alcohol (ethanol or isopropanol). Thus, the use of an alcohol as an additive to propylene oxide sterilisation with aldehyde cross-linked tissues (containing residual aldehydes) could result in elevated aldehyde levels, which in turn increases the calcification potential of these tissues and ultimately bioprosthetic failure.

Consequently, what is required is an efficient sterilization process which not only sterilizes chemical cross-linked collagen-based biomaterials, but also provides a convenient storage medium for the sterilized biomaterial.

SUMMARY

The inventors have developed a process that overcomes or at least alleviates the problems associated with typically used sterilization and/or storage methods for cross-linked collagen-based biomaterials.

Accordingly, in a first aspect the present invention provides a method for sterilizing a cross-linked collagen-based biomaterial comprising contacting said cross-linked collagen-based biomaterial with a sterilization solution comprising between 3% and 6% v/v propylene oxide and incubating said biomaterial between 30° C. and 55° C. for greater than 48 hours; with the proviso that the sterilization solution does not include alcohol.

In some embodiments the incubation temperature is between 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C. and 55° C. In other embodiments the incubation temperature is between 30° C. and 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C. or 55° C. In other words, all combinations of temperatures between the range 30° C. and 55° C. are envisaged. In some embodiments the incubation temperature is preferably between 35° C. and 50° C., more preferably between 40° C. and 48° C. In some embodiments the incubation temperature is about 45° C.

Once the incubation period has lapsed i.e. more than 48 hours have elapsed it is permissible to allow the temperature to reduce to room temperature. Indeed, the sterilized cross-linked collagen-based biomaterial can remain at room temperature for some time after the initial 48 hours as at this time. Once the sterilized cross-linked collagen-based biomaterial has been incubated in the propylene oxide for at least 4 days the propylene oxide will have been converted to propylene glycol and the collagen-based biomaterial will be ready to use.

In some embodiments, the sterilization solution comprises between 3.8% and 4.5% v/v propylene oxide. In other embodiments, the sterilization solution comprises about 4% v/v propylene oxide. In some embodiments, the sterilization solution consists essentially of between 3% and 6% v/v propylene oxide, more preferably the sterilization solution consists of between 3% and 6% v/v propylene oxide. In some embodiments, the sterilization solution consists essentially of between 3.8% and 4.5% v/v propylene oxide, more preferably the sterilization solution consists of between 3.8% and 4.5% v/v propylene oxide. In some embodiments, the sterilization solution consists essentially of about 4% v/v propylene oxide, more preferably the sterilization solution consists of about 4% v/v propylene oxide.

It will be appreciated that alcohol, especially ethanol and/or isopropanol is not used in the sterilization solution of the present invention.

It is a requirement that the sterilization step is carried out for greater than 48 hours (2 days); however, as the sterilization solution can also be used as a storage medium the sterilization step can be carried out for 2, 3, 4, 5, 6, 7, 8, 9, 10 or more days.

The cross-linked collagen-based biomaterial can be any material which comprises, consists essentially of or consists of collagen. In some embodiments, the collagen-based biomaterial is isolated directly from an animal. The biomaterial can be isolated from any animal, whether from the same species as a recipient or from an animal of a different species to the recipient. Preferably, the animal is from one of the mammalian orders i.e. *Artiodactyla, Lagomorpha, Rodentia, Perissodactyla, Carnivora* and *Marsupialia*. More preferably, the animal is selected from the group consisting of an ovine, a bovine, a caprine, an equine, a porcine, a marsupial and a human.

The biomaterial may be any type of cellular tissue. Preferably, the cellular tissue is selected from the group consisting cardiovascular tissue, heart tissue, heart valve, aortic roots, aortic wall, aortic leaflets, pericardial tissue, connective tissue, dura mater, dermal tissue, a vascular tissue, cartilage, pericardium, ligament, tendon, blood vessels, umbilical tissue, bone tissue, fasciae, and submucosal tissue and skin.

In some embodiments, the biomaterial is and/or comprises discrete i.e. isolated collagen, rather than a naturally-occurring collagen-containing tissue. The discrete collagen may be used in its isolated state or formed into any medical device or article known in the art.

In some embodiments, the biomaterial is a cultured tissue, a prosthesis containing extra-cellular matrix obtained from an animal, a reconstituted tissue (e.g. collagen matrix), or the like.

It will also be appreciated that the biomaterial might further comprise synthetic analogs formed from synthetic polymers, biological polymers, or both, including those generally found in natural tissue matrices. Suitable synthetic polymers include, for example, polyamides and polysulphones. Biological polymers can be naturally occurring or produced in vitro by, for example, fermentation and the like.

In a second aspect, the present invention provides a method for sterilizing a collagen-based biomaterial comprising:

(a) providing a collagen-based biomaterial and washing same with ice-cold 0.9% v/v saline solution and placing said biomaterial in ice-cold 0.9% v/v saline/Phenyl-methyl-sulfonyl-fluoride (PMSF);

(b) contacting said collagen-based biomaterial with 0.625% v/v glutaraldehyde solution and potassium di-hydrogen phosphate pH 7.4 and incubating same at about 1-5° C. for at least 5 days to produce a cross-linked collagen-based biomaterial;

(c) rinsing said cross-linked collagen-based biomaterial in sterile 0.9% v/v sodium chloride at approximately 10° C. and then contacting the cross-linked collagen-based biomaterial with a sterilization solution comprising between 3.8% and 4.5% v/v propylene oxide and incubating said tissue between 30° C. and 55° C. for greater than 48 hours; with the proviso that the sterilization solution does not include alcohol.

In a third aspect the present invention provides a method for storing a sterilized, cross-linked collagen-based biomaterial comprising contacting a cross-linked collagen-based biomaterial with a solution comprising between 3% and 6% v/v propylene oxide and incubating said biomaterial between 30° C. and 55° C. for greater than 48 hours and then allowing the biomaterial to remain in contact with said propylene oxide until same converts to propylene glycol; with the proviso that the solution does not include alcohol.

In a fourth aspect, the present invention provides a sterilized, cross-linked collagen-based biomaterial produced by a method according to the first, second or third aspects.

It will be appreciated that once the sterilized, cross-linked collagen-based biomaterial has been obtained by the methods of the present invention it can be included with implantable biological devices. Accordingly, in a fifth aspect, the present invention provides an implantable biological device comprising a sterilized, cross-linked collagen-based biomaterial according to the fourth aspect.

In a further aspect of the present invention the cross-linked collagen-based biomaterial of the present invention is contained within a kit for repairing a tissue injury. Thus, in a sixth aspect the present invention provides a kit for repairing a tissue injury comprising:

(a) a sterile container having a sterilized, cross-linked collagen-based biomaterial according to the fourth aspect or a device according to the fifth aspect; and (b) instructions for use on an injured subject.

In a seventh aspect, the present invention provides a container comprising a sterilized, cross-linked collagen-based biomaterial and a 3% to 6% v/v propylene glycol solution, wherein said propylene glycol has resulted from the conversion in situ of a 3% to 6% v/v propylene oxide solution while in the presence of the biomaterial.

The collagen-based biomaterial of the present invention may be cross-linked by any method know in the art of cross-linking collagen including, but not limited to, the methods disclosed in Eyre et al., 1984, *Annu. Rev. Biochem.* 537, 717-748; Eyre, 1982, In: Symposium on Heritable Disorders of Connective Tissue (Akeson et al. eds) pp. 43-58, Mosby, St. Louis, Mo.; Davison & Brennan, 1983, *Connect. Tissue Res.* 11, 135-151; Robins, 1982, *Methods Biochem. Analysis,* 28, 330-379; Reiser, 1991, *Proc. Soc. Exp. Biol. Med.* 196, 17-29; all of which are incorporated herein in their entirety by reference. However, a preferred method of cross-linking the collagen-based biomaterial of the present invention comprises:

(a) exposing a collagen-based biomaterial to an alcohol-containing solution for at least 24 hours;

(b) exposing said biomaterial in step (a) to a cross-linking agent; and (c) exposing said biomaterial in step (b) to an acidic solution; wherein step (b) and (c) are sequential to step (a).

The alcohol-containing solution used in step (a) is preferably a water-based liquid i.e. is an aqueous solution of greater than about 50% v/v alcohol, and preferably between 60% to 80% alcohol by volume. Either buffered or non-buffered alcohol-containing solution can be used; however, it is preferable that a non-buffered alcohol-containing solution is used as it has been found that buffered alcohol-containing solutions adversely affect subsequent cross-linking procedures producing a yellowed biomaterial.

The preferred method of cross-linking can use any alcohol known in art in the alcohol-containing solution. Preferably, the alcohol is a $C_1$-$C_6$ lower alcohol in a buffer-free solution. Even more preferably, the alcohol is selected from the group consisting of methanol, ethanol, cyclohexanol, isopropanol, propanol, butanol, pentanol, isobutanol, sec-butanol and t-butanol.

In some embodiments, the alcohol-containing solution comprises a mixture of two or more alcohols provided that the combined volume of the alcohol is greater than 50% v/v. For example, a mixture of about 70% v/v ethanol and about 10% v/v isobutanol is effective.

The biomaterial in step (a) can be exposed to the alcohol-containing solution for any length of time as long as it is sufficient to render the biomaterial resistant to in vivo pathogenic calcification. Preferably, the biomaterial remains in contact with the alcohol-containing solution for sufficient time to enable the alcohol to diffuse and permeate into the biomaterial. More preferably, the biomaterial is exposed to the alcohol-containing solution for at least 24 hours, even more preferably at least 36 hours and most preferably, at least 48 hours.

The biomaterial, after exposure to the alcohol-containing solution, is removed and exposed to one or more cross-linking agents. Any form of cross-linking agent known in the art or combination thereof may be used as long as it is capable of cross-linking collagen. Accordingly, it will be appreciated that cross-linking agents, include but are not limited to, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light (e.g., blue light and UV light), pH, temperature, and combinations thereof. Preferably, the cross-linking agent is a chemical cross-linking agent selected from the group consisting of carbodiimide, polyepoxy ethers, divinyl sulfone (DVS), polyaldehyde and diphenylphosphoryl azide (DPPA).

In some embodiments, the polyaldehyde is a bi-, tri- or di-aldehyde. Glutaraldehyde is especially preferred.

In some embodiments, the cross-linking step (b) is followed by step (c), with or without an intervening wash step. The acidic solution used in step (c) contains any acid capable of inactivating and/or modifying the fixed and/or unfixed cross-linking agent moieties present in the biomaterial after step (b) to remove or reduce available calcium binding sites. Alternatively, or in addition to, the acidic solution used in step (c) contains any acid capable of further cross-linking the activated carboxyl groups with the activated amine groups on the collagen to form amide bonds. Preferably, the acid in the acidic solution comprises an aminocarboxylic acid. Preferably, the aminocarboxylic acid is an acid having at least one amino group and at least one carboxylic acid substituent. More preferably, the aminocarboxylic acid is selected from the group consisting of L-arginine, L-lysine, L-histidine, L-glutamate or L-aspartate.

The step of rinsing the biomaterial is conducted using a phosphate-free solution of 0.9% v/v saline.

While it will be appreciated by those skilled in the art that the temperature at which each of the steps in the preferred cross-linking method is carried out is not critical, it will be understood that preferably, the temperature is between 2° C. and 40° C., more preferably, between 4° C. and 30° C. and most preferably, between 5° C. and 25° C.

In one embodiment, the alcohol, acidic solution and rinsing solution are all buffer-free.

DETAILED DESCRIPTION OF THE PREFERRED EMBODIMENTS

Figure 1:
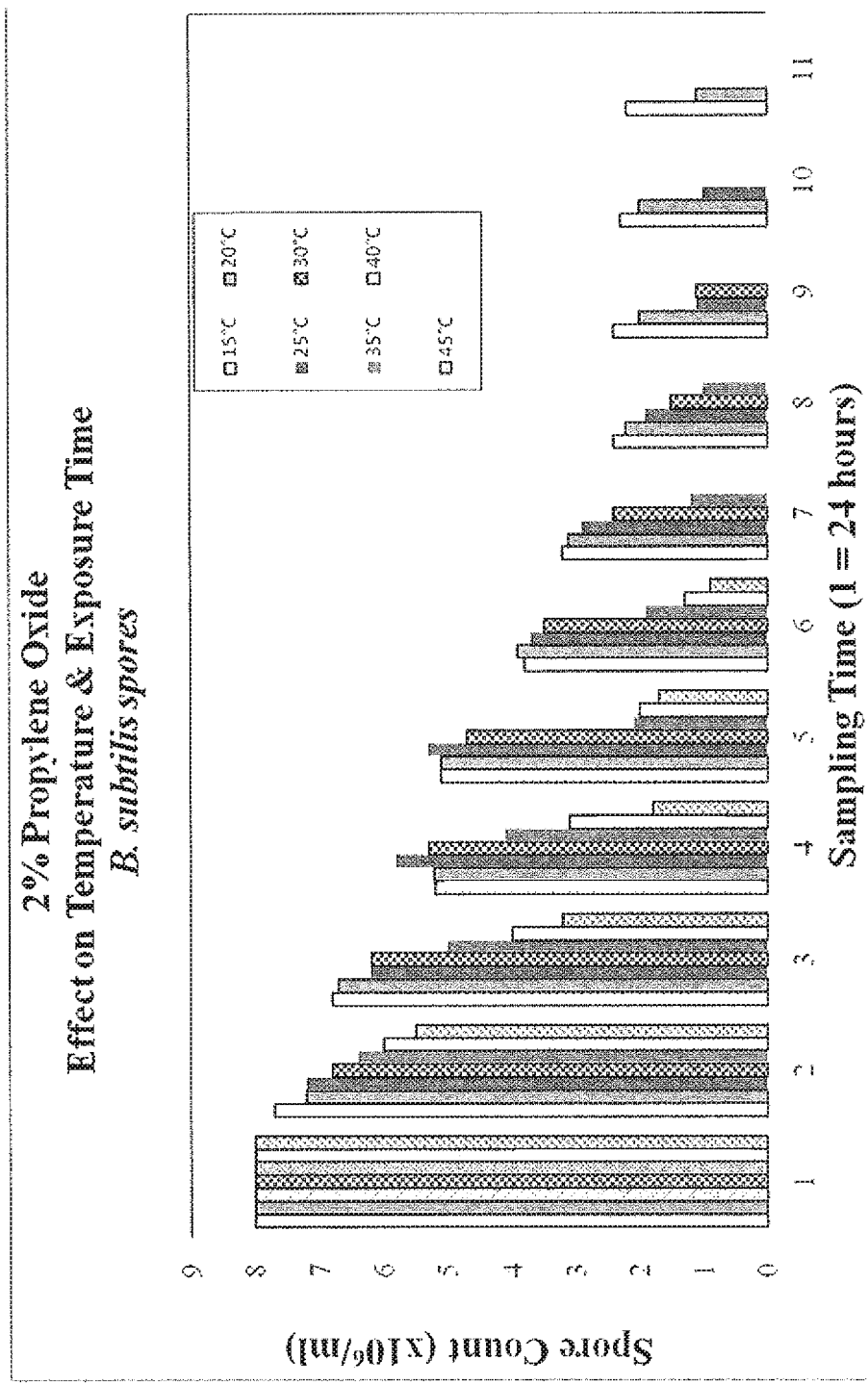
FIG. 1 shows the effect of 2% propylene oxide at varying temperatures between 15° C. and 45° C. on *B. subtilis* spores over time.

Before describing the present invention in detail, it is to be understood that this invention is not limited to particularly exemplified methods of production, which may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional immunological techniques, chemistry and pharmacology within the skill of the art. Such techniques are well known to the skilled worker, and are explained fully in the literature. See, e.g., Coligan, Dunn, Ploegh, Speicher and Wingfield "Current protocols in Protein Science" (1999) Volume I and II (John Wiley & Sons Inc.); and Bailey, J. E. and Ollis, D. F., Biochemical Engineering Fundamentals, McGraw-Hill Book Company, NY, 1986; Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

It must be noted that as used herein and in the appended claims, the singular forms "a," "an," and "the" include plural reference unless the context clearly dictates otherwise.

Thus, for example, a reference to "a cross-linking agent" includes a plurality of such agents, and a reference to "an alcohol" is a reference to one or more alcohols, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In one of the broadest aspects, the present invention relates to a method for sterilizing a collagen-based biomaterial.

As used herein, the term "biomaterial" refers to any collagen containing material that potentially has a biological use. The collagen might be any type of collagen from any source and might be present alone or in combination with other materials. Accordingly, the collagen might represent as little as 1% w/w of the total weight of the biomaterial or as much as 100%.

The term "collagen" as used herein refers to the extracellular family of fibrous proteins that are characterised by their stiff, triple-stranded helical structure. Three collagen polypeptide chains ("α-chains") are wound around each other to form this helical molecule. The term is also intended to encompass the various types of collagen.

The major portion of the helical portion of collagen varies little between mammalian species. Indeed, a number of collagen types have high degrees of nucleotide and amino acid sequence homologies. For example, the nucleotide sequence homology for collagen alpha I type II is at least 88% when comparing humans, equines and murine. Humans and equines have 93% sequence homology at the nucleotide level, while mouse and equine have 89% sequence homology. The nucleotide sequence homology for human and mouse is 88% (see, NCBI accession numbers U62528 (Equine), NM033150 (Human) and NM031163 (mouse) http://www.ncbi.nlm.nih.gov). Other types of collagen have similar levels of amino acid homology. For example, the nucleotide sequence homology between porcine collagen alpha I type I and ovine collagen alpha I type I is 90% (see, NCBI accession numbers AF29287 (Ovine) and AF201723 (Porcine) http://www.ncbi.nlm.nih.gov).

Given the level of common ancestry and biology for many of the above animals, the high degree of amino acid and nucleotide sequence homology for collagen across a number of species such as cattle, sheep, mice and pigs, a person skilled in the art would appreciate that the methods for producing the biomaterial as disclosed herein are applicable for collagenous material isolated from all mammalian animals.

Accordingly, in some embodiments, the biomaterial is isolated or harvested from an animal of one of the mammalian orders i.e. *Artiodactyla, Lagomorpha, Rodentia, Perissodactyla, Carnivora* and *Marsupialia*. The animal is preferably an ovine, a bovine, a caprine, an equine, a porcine, a marsupial or a human. While the biomaterial is preferably isolated from the same animal species as the recipient, it is envisaged that the biomaterial might be isolated from a different species to the recipient.

Alternatively, in some embodiments, the biomaterial comprises a cultured tissue, a reconstituted tissue or the like.

The biomaterial might be any type of cellular tissue. For example, the cellular tissue might be cardiovascular tissue, pelvic floor tissue, heart tissue, heart valve, aortic roots, aortic wall, aortic leaflets, pericardial tissue, connective tissue, the matrix of soft or solid organs, dermal tissue, a vascular tissue, dura mater, cartilage, pericardium, ligament, tendon blood vessels, umbilical tissue, bone tissue, fasciae, and submucosal tissue or skin as all of these comprises some collagen.

It will also be appreciated that the biomaterial might further comprise synthetic analogs formed from synthetic polymers, purified biological polymers, or both, including those generally found in natural tissue matrices. Suitable synthetic polymers include, for example, polyamides and polysulphones. Biological polymers can be naturally occurring or produced in vitro by, for example, fermentation and the like.

Purified biological polymers can be appropriately formed into a substrate by techniques such as weaving, knitting, casting, moulding, extrusion, cellular alignment, and magnetic alignment. Suitable biological polymers include, without limitation, collagen, elastin, silk, keratin, gelatin, polyamino acids, polysaccharides (e.g. cellulose and starch), and copolymers of any of these. For example, collagen and elastin polymers can be formed into a synthetic implantable material by any of a variety of techniques, such as weaving and moulding. Synthetic tissue analogs mimic a natural tissue matrix. Alternatively, synthetic substrates can be used to form a tissue analog, either alone or together with naturally occurring substrates Non-limiting examples include, polypropylene, polylactic acid, polyester, nylon, silicone and the like.

Once the biomaterial has been acquired it is cross-linked The cross-linking can utilize any of the well known procedures including, but not limited to, those described in Eyre et al., 1984, *Annu. Rev. Biochem.* 537, 717-748; Eyre, 1982, In: Symposium on Heritable Disorders of Connective Tissue (Akeson et al. eds) pp. 43-58, Mosby, St. Louis, Mo.; Davison & Brennan, 1983, *Connect. Tissue Res.* 11, 135-151; Robins, 1982, *Methods Biochem. Analysis* 28, 330-379; Reiser, 1991, *Proc. Soc. Exp. Biol. Med.* 196, 17-29.

A preferred method of cross-linking is disclosed in the Applicants International Patent Application WO2006/066327 incorporated herein in its entirety by reference. Briefly, an initial step in the preferred method of cross-linking the collagen-based biomaterial of the present invention comprises contacting the biomaterial with an alcohol-containing solution. As used herein, the term "contacted," or "contacting" refers to the active step of immersing the collagen-based biomaterial in a solution or agent as described here, or as described infra, subsequently contacting the biomaterial with a cross-linking agent, an acidic solution or other matter for a sufficient period of time to bring about a desired outcome. Methods for contacting the biomaterial with, for example, the alcohol-containing solution are well known in the art. For example, in general, the biomaterial can be contacted by spraying, dipping or immersing the biomaterial in a solution or agent.

The term "alcohol" as used herein refers to any alcohol known in art which is capable of removing or reducing the amount of triglycerides and at least partially esterifying the carboxyl groups found on collagen. Preferably, the alcohol is a water-soluble alcohol. More preferably, the alcohol is a $C_1$-$C_6$ lower alcohol in a buffer-free solution. Even more preferably, the alcohol is selected from the group consisting of methanol, ethanol, cyclohexanol, isopropanol, propanol, butanol, pentanol, isobutanol, sec-butanol and t-butanol.

Without wishing to be bound by any particular theory or hypothesis the inventors consider that the alcohol-containing solution assists in loosening the collagen triple helix and thereby exposing hydrophobic sites (see, Karube & Nishida, 1979, *Biochim Biophys Acta.,* 23; 581(1): 106-13). They also consider that the carboxyl and amine groups found in collagen are esterified in the presence of the alcohol-containing solution such that they become available for cross-linking in later steps. As such, a preferred alcohol solution is one comprising at least about 50% v/v, more preferably at least about 70% v/v and most preferably at least about 80% v/v alcohol to buffer-free aqueous solution. In one embodiment, the alcohol solution is 70% ethanol v/v in 0.9% saline (containing 0.5 mM PMSF)

In some embodiments the alcohol-containing solution, as well as other solutions and reagents used herein are "buffer-free" as it is hypothesised that the cross-linking agents containing aldehyde reacts with the buffer during fixation causing depolymerization of the aldehyde.

The step of contacting the biomaterial to the alcohol-containing solution may be carried out for any length of time as long as it is sufficient to render the biomaterial resistant to in vivo pathogenic calcification and that the majority (i.e. a high percentage) of the carboxyl and amine groups found in collagen are esterified. Preferably, the biomaterial remains in contact with the alcohol-containing solution for sufficient time to enable the alcohol to diffuse and permeate into the biomaterial. More preferably, the biomaterial is exposed to the alcohol-containing solution for at least 24 hours, even more preferably at least 36 hours and most preferably, at least 48 hours.

Once the collagen-based biomaterial has been exposed to alcohol it is removed. In some embodiments, the biomaterial is rinsed after the exposure to alcohol in a rinsing solution comprising a phosphate-free solution of 0.9% v/v saline. However, any non-buffered physiologically acceptable solution may be used as a rinsing solution. The purpose of the rinsing solution is mainly to remove excess alcohol and as such is not critical.

After the collagen-based biomaterial has been exposed to alcohol for greater than 24 hours it is then contacted with one or more cross-linking agents, especially bifunctional cross-linking agents. The term "bifunctional" as used herein refers to the two functional aldehyde groups, present at both ends of the five carbon chain. The cross-linking can be undertaken by any technique known in the art, with any form of cross-linking agent as long as it is capable of cross-linking collagen. Cross-linking agents, include but are not limited to, acylating compounds, adipyl chloride, aldehydes, alkyl and aryl halides, bisimidates, carbodiimides, divinyl sulfone (DVS), formaldehyde, glutaraldehyde, glyoxal, hexamethylene diisocyanate, hydroxychloride, hydroxyethyl methacrylate divinyl sulfone (HEMA-DIS-HEMA), imidoesters, isocyanates, light (e.g. blue light and UV light), N-hydroxysuccinimide, N-substituted maleimides, pH, polyaldehyde, diphenylphosphoryl azide (DPPA), polyepoxy compounds comprising backbone of 17-25 carbons and 4-5 epoxy groups, polyepoxy ethers, polyethylene glycol divinyl sulfone (VS-PEG-VS), polyglycerol polyglycidyl ether and temperature and combinations thereof.

In some embodiments, the cross-linking agent is a chemical cross-linking agent such as carbodiimide, polyepoxy ethers, divinyl sulfone (DVS), genipin, glutaraldehyde, formaldehyde and diphenylphosphoryl azide (DPPA).

It has also been demonstrated that polyepoxy compounds comprising backbone of 17-25 carbons and 4-5 epoxy groups show a high efficiency for the cross-linking collagen (see, for example, US Pat. Applic. No. 20040059430 (Ser. No. 10/618,447). It has also been shown that the toxicity of polyepoxy compounds is lower than that of glutaraldehyde, and the antigenicity or immune-response induction of tissues decreases in proportion to the reaction time, in case of reacting with helical polypeptide molecules such as collagen. Naturally, it shows relatively good biocompatibility (see, for example, Lohre et al., (1992), *Artif. Organs*, 16:630-633; Uematsu et al., (1998), *Artif. Organs*, 22:909-913). Consequently, polyepoxy compounds as described are one preferred cross-linking agent.

In some embodiments, the cross-linking agent comprises about 1% glutaraldehyde and the length of exposure is at least about 24 hours. It will be appreciated that the time length for exposure of the biomaterial to the cross-linking agent depends on the agent used, the concentration and the temperature. Typically, the length of exposure is between 24 hours to 28 days. The determination of the precise amount of exposure time for the biomaterial to the cross-linking agent is well within the scope of a person skilled in the art.

Again, without wishing to be bound by any particular theory or hypothesis, the inventors consider that by exposing the collagen-based biomaterial that has been exposed to alcohol to a cross-linking agent, the esterified carboxyl groups and amine groups on the collagen present in the biomaterial are cross-linked.

While it will be appreciated by those skilled in the art that the temperature at which each of the steps of the preferred cross-linking method is carried out is not critical, it will be understood that preferably, the temperature is between 2° C. and 40° C., more preferably, between 4° C. and 30° C. and most preferably, between 5° C. and 25° C.

Once again, after the cross-linking step, the collagen-based biomaterial is preferably rinsed in rinsing solution such as that used after the alcohol exposure step (a). However, it will again be appreciated that the rinsing step is merely a preferment.

Following the cross-linking step, or if utilised, the rinsing step after the cross-linking step, the collagen-based biomaterial may then be sterilized for use by the methods described herein. Alternatively, the collagen-based biomaterial is contacted with an acidic solution containing any acid capable of inactivating and/or modifying the fixed and/or unfixed cross-linking agent moieties present in the biomaterial after step (b) to remove or reduce available calcium binding sites. Alternatively, or in addition to, the acidic solution used in step (c) contains any acid capable of further cross-linking the activated carboxyl groups with the activated amine groups on the collagen to form amide bonds.

Preferably, the acidic solution comprises at least one aminocarboxylic acid. The term "aminocarboxylic acid" as used herein is any acid having at least one amino group and at least one carboxylic acid substituent. Representative examples of aminocarboxylic acids that are useful in the present invention include, but are not limited to, L-glutamate, L-aspartate, L-lysine L-arginine, L-histidine. The purpose of the acidic solution is two-fold: firstly, the aminocarboxylic acid assists in the inactivation and/or modification of the fixed and unfixed cross-linking agent moieties, thereby reducing or alleviating any adverse biological effects. Secondly, the aminocarboxylic acid further cross-links the activated carboxyl groups with the activated amine groups on the collagen to form amide bonds.

The concentration of the aminocarboxylic acid will depend upon the actual acid used and other parameters such as total mass of the biomaterial used and the like. In addition, a minimum wet weight ratio of aminocarboxylic acid to biomaterial would be about 1:4. The most important aspect of the acidic solution is the pH. The pH must be below pH7, preferably below pH6, more preferably below pH5 and most preferably below about pH4.6.

In one embodiment, the acidic solution is 8 mg aminocarboxylic acid per millilitre of de-ionised water, which is phosphate-free and about pH4.

The cross-linked collagen-based biomaterial is exposed to the aminocarboxylic acid for at least 6 hours, more preferably at least 24 hours, even more preferably more than 48 hours. While the incubation temperature is not critical it is preferably between 5° C. and 55° C., more preferably between 10° C. and 45° C., most preferably about 45° C.

In some embodiments, step (c) of the disclosed cross-linking method is replaced by or supplemented with a method of inhibiting the formation of metalloproteinase on elastin molecules present in the biomaterial. Specifically, in tissue such as aortic tissue a higher percentage of elastin is present than in other tissue. These elastin molecules can provide sites for the formation of metalloproteinase as such these sites need to be reduced, removed or inactivated.

The cross-linked collagen-based biomaterial, before or after the step of exposing the biomaterial to the acidic solution and/or buffer-free solution containing a multi-valent cation, is again preferably rinsed in rinsing solution. The cross-linked collagen-based biomaterial is then sterilized.

The step of sterilizing the biomaterial comprises contacting the cross-linked collagen-based biomaterial with a sterilization solution comprising between 3% and 6% v/v propylene oxide and incubating said biomaterial between 30° C. and 55° C. for greater than 48 hours; with the proviso that the sterilization solution does not include alcohol.

It will be appreciated that alcohol, especially ethanol and/or isopropanol is not used in the sterilization solution of the present invention.

It has been well established that at elevated temperatures eg above 55° C., collagen undergoes intracellular degradation. Indeed, it has been shown that collagen within human skin fibroblasts starts to undergo increased degradation at temperatures above 41° C. (Palotie, 1983, *Coll Relat Res. March;* 3(2): 105-13). Thus, in sterilizing the cross-linked collagen-based biomaterial of the present invention the temperature of incubation is a critical factor. The temperature is preferably not greater than 55° C. as this increases the chance that the collagen begins to degrade. However, as described in Example 9 and elsewhere, it is important that the incubation temperature is not less than 30° C. as temperatures lower than 30° C. have reduced sterilization potential.

It will be appreciated by persons skilled in the art that concentrations of propylene oxide below 3% would not provide sufficient sterilization as defined herein. Concentrations of propylene oxide above 6% are toxic and have an adverse effect on the integrity of the biomaterial. In some embodiments, the sterilization solution comprises between 3.8% and 4.5% propylene oxide. In other embodiments, the sterilization solution comprises about 4% propylene oxide. In some embodiments, the sterilization solution consists essentially of between 3% and 6% propylene oxide, more preferably the sterilization solution consists of between 3% and 6% propylene oxide. In some embodiments, the sterilization solution consists essentially of between 3.8% and 4.5% propylene oxide, more preferably the sterilization solution consists of between 3.8% and 4.5% propylene oxide. In some embodiments, the sterilization solution consists essentially of about 4% propylene oxide, more preferably the sterilization solution consists of about 4% propylene oxide.

The term "about" as used herein refers to a deviation in the value following the term by 10% above or below. For example, reference to about 4% propylene oxide includes ranges between 3.6% and 4.4% i.e. 10% below or above the 4% value. This includes 3.7%, 3.8%, 3.9%, 4.0%, 4.1%, 4.2%, 4.3% and 4.4% propylene oxide.

It is a requirement that the sterilization step is carried out for greater than 48 hours; however, as described herein propylene oxide can also be used as a storage media and as such the sterilization step can be carried out for at least 2, 3, 4, 5, 6, 7, 8, 9, 10 days or more.

One major benefit of the methods described herein is that the sterilization solution used herein i.e between 3% and 6% v/v propylene oxide will not only sterilize collagen-containing tissue without affecting the collagen fibrils, but as propylene oxide converts after about 4 days being in contact with the biomaterial to propylene glycol (which is not toxic), the sterilized cross-linked collagen-based biomaterial can remain in the sterilization solution well after the initial 48 hours. Indeed, it is envisaged that the cross-linked collagen-based biomaterial will be sterilized and stored and then shipped in the same container to the end customer without the need for further handling.

The term "sterilization" as used herein means that the cross-linked collagen-based biomaterial satisfies the requirements under ISO 14160. ISO 14160 covers the sterilization of health care products and pertains to liquid chemical sterilizing agents for single-use medical devices utilizing animal tissues and their derivatives. Briefly, ISO 14160 requires tissues to be inoculated with *B. subtilis* spores and then treated to remove the contamination. The requirements for ISO 14160 trials are described in Example 6 supra.

In some embodiments, the sterilization solution is buffer-free. In other embodiments the solution comprises de-ionized water.

The cross-linked collagen-based biomaterial, after treatment with the methods disclosed herein, has a high level of resistance to calcification i.e. it is a "calcification-resistant biomaterial". The term "calcification" as used herein refers to one of the major pathological problems associated with traditionally produced biomaterial comprising connective tissue proteins (i.e., collagen and elastin). It has previously been shown that these materials can become calcified following implantation within the body. Such calcification can result in undesirable stiffening or degradation of the biomaterial. Two (2) types of calcification: intrinsic and extrinsic are known to occur in fixed collagenous biomaterial, although the exact mechanism(s) by which such calcification occurs is unknown. Intrinsic calcification is characterised by the precipitation of calcium and phosphate ions within the fixed bioprosthetic tissue, including the collagen matrix and remnant cells. Extrinsic calcification is characterised by the precipitation of calcium and phosphate ions within adherent thrombus, including adherent cells (e.g., platelets) to the biomaterial and the development of calcium phosphate-containing surface plaques on the biomaterial.

Consequently, the phrase "high level of resistance to calcification" or "calcification-resistant" when applied to the biomaterial of the present invention means that the biomaterial, after in vivo implantation for at least 200 days, shows less than 50 µg, preferably less than 20 µg, and even more preferably less than 10 µg of calcium per mg of dried tissue after its removal.

Preferably, the biomaterial of the present invention is also resistant to enzymatic degradation. The term "resistant to enzymatic degradation" as used herein refers to the ability of the biomaterial of the present invention to withstand enzymatic degradation to a comparable level with traditional fixed tissue.

Once formed, the sterilized, cross-linked collagen-based biomaterial of the present invention can then be used to treat a number of conditions and/or disorders.

Generally, the terms "treating," "treatment" and the like are used herein to mean affecting an individual or animal, their tissue or cells to obtain a desired pharmacological and/or physiological effect. The effect is especially therapeutic in terms of a partial or complete cure of a condition and/or disorder. "Treating" as used herein covers any treatment of a condition and/or disorder in a vertebrate, a mammal, particularly a human, and includes: (a) inhibiting the condition and/or disorder, i.e., arresting its development; or (b) relieving or ameliorating the symptoms of the condition and/or disorder, i.e., cause regression of the symptoms of the enzymatic degradation/condition and/or disorder.

The terms "condition" and/or "disorder" are used herein interchangeably and refers to abnormal conditions affecting animals, including humans, which can be treated using the biomaterial of the present invention. Accordingly, the treatment of a wound, a lesion, tissue degeneration, a microbial infection, a burn, an ulcer, dermal condition is included in the present invention. Moreover, the replacement of heart valves, aortic roots, aortic wall, aortic leaflets, pericardial tissue, connective tissue, dura mater, dermal tissue, a vascular tissue, cartilage, pericardium, ligaments, tendon blood vessels, umbilical tissue, bone tissue, fasciae, and submucosal tissue are also encompassed.

The calcification-resistant biomaterial of the present invention may also be applied to any of a wide variety of contacting surfaces of medical devices. Contacting surfaces include, but are not limited to, surfaces that are intended to contact blood, cells or other bodily fluids or tissues of an animal, including specifically a human. Suitable contacting surfaces include one or more surfaces of medical devices that are intended to contact blood or other tissues. The medical devices include aneurysm coils, artificial blood vessels, artificial hearts, artificial valves, artificial kidneys, artificial tendons and ligaments, blood bags, blood oxygenators, bone and cardiovascular replacements, bone prostheses, bone waxes, cardiovascular grafts, cartilage replacement devices, catheters, contact lenses, containers for cell and tissue culture and regeneration, embolization particles, filtration systems, grafts, guide channels, in-dwelling catheters, laboratory instruments, microbeads, nerve-growth guides, ophthalmic implants, orthopedic implants, pacemaker leads, probes, prosthetics, shunts, stents, supports for peptides, surgical instruments, sutures, syringes, urinary tract replacements, wound coverings, wound dressings, wound healing devices and other medical devices known in the art.

Other examples of medical devices that would benefit from the application of the present invention will be readily apparent to those skilled in the art of surgical and medical procedures and are therefore contemplated by the instant invention. The contacting surface may include a mesh, coil, wire, inflatable balloon, or any other structure which is capable of being implanted at a target location, including intravascular locations, intralumenal locations, locations within solid tissue, and the like. The implantable device can be intended for permanent or temporary implantation. Such devices may be delivered by or incorporated into intravascular and other medical catheters.

The process of coating the surfaces of such devices can be performed by the plasma coating technique, as described in the International patent application No. WO96/24392.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention will now be further described by way of reference only to the following non-limiting examples. It should be understood, however, that the examples following are illustrative only, and should not be taken in any way as a restriction on the generality of the invention described above.

EXAMPLE 1

Basic Processing and Storage of Biomaterial

Harvesting of a Collagen-Derived Biomaterial

Porcine hearts from adult pigs were harvested at a local abattoir and transported to the laboratory on ice packs within 2-4 hours of death. The hearts were washed twice in ice-cold 0.9% v/v saline solution and carefully cleaned from adherent fat and loose connective tissue. The aortic roots with the aortic valves were dissected from the hearts and placed in ice-cold 0.9% v/v saline/Phenyl-methyl-sulfonyl-fluoride (PMSF) and the valved aortic roots washed for 20 minutes in the 0.9% v/v saline solution containing PMSF. The valve leaflets were removed from the aortic valve orifice and stored in ice-cold 0.9% v/v saline solution.

Cross-Linking (Fixation) of the Biomaterial

A 0.625% v/v glutaraldehyde solution containing 9.07 g/l potassium di-hydrogen phosphate buffer in sterile, deionised water was prepared. The pH of the glutaraldehyde solution was adjusted to 7.4 with sodium hydroxide. The aortic valve leaflets were cross-linked in the glutaraldehyde solution at 1-5° C. for a minimum period of 5 days to crosslink proteins present in the collagen of the tissues.

Rinsing the Cross-Linked Biomaterial

The aortic valve leaflets were removed from the glutaraldehyde solution and rinsed in a sterile 0.9% v/v sodium chloride for about 15 minutes. During the rinsing period, the temperature of the rinsing solution was maintained at approximately 10° C.

Final Sterilization and Storage of the Biomaterial

The porcine aortic valve leaflets were immersed in a 2.0% v/v solution of glutaraldehyde containing 29.02 g/l potassium di-hydrogen phosphate buffer in sterile, deionised water. The pH of the aldehyde solution was adjusted to 7.4 with sodium hydroxide. The process of sterilization was carried out at about 25° C. for 5 days. The sterilized tissues were divided into four groups and stored in: (i) 0.625% v/v glutaraldehyde, (ii) 5.0% v/v glutaraldehyde, (iii) 10% v/v glutaraldehyde; and (iv) 2% v/v propylene oxide until further use.

EXAMPLE 2

Effect of Storage Solution on Calcification Profile of Biomaterial

Experimental studies in small and large animal models were conducted to assess the effectiveness of the above-described sterilisation-storage process in mitigating calcification of treated collagen containing biomaterials.

In the first animal study, porcine aortic valve leaflets sterilised and stored according to the methods described in Example 1 were used for assessment in a small animal model.

Sterilised and stored porcine aortic valve leaflets of all four groups were rinsed in 0.9% v/v saline for 5 minutes. The rinsed tissues were surgically implanted in subcutaneous pockets (one sample of each group per rat), created in the central abdominal wall area of growing (6 weeks old) male Wistar rats. These tissues were removed after 60 days, host tissue removed and samples dried in a Biotherm™ incubator (Marcus Medical, JHB, RSA) at 90° C. for 48 h.

The dried samples were weighed, and the calcium content extracted in 5.0 ml 6 N ultrapure hydrochloric acid (Merck, JHB, RSA) at 75° C. for 24 h. The extractable calcium content was then measured using an atomic absorption spectrophotometer (Varian AA1275) and expressed as µg calcium per mg tissue (dry weight). These data are summarised in Table 1. Results (µg Calcium per mg dried tissue) are summarised in Table 1.

TABLE 1

| Storage solution | Mean ± standard error |
| --- | --- |
| Glutaraldehyde (0.625%) | 70.146 µg Ca/mg Tissue ± 7.037 |
| Glutaraldehyde (5.0%) | 88.439 µg Ca/mg Tissue ± 4.470 |
| Glutaraldehyde (10.0%) | 66.870 µg Ca/mg Tissue ± 13.235 |
| Propylene Oxide (2.0%) | 25.311 µg Ca/mg Tissue ± 5.292 |

EXAMPLE 3

Effect of Sterilization & Storage Solution on Calcification Profile of Biomaterial Harvesting of a Collagen-Derived Biomaterial In the second animal study, porcine aortic valve leaflets were harvested and isolated according to the method described in Example I. Isolated porcine aortic valve leaflets were divided into three groups. Group I received a typical cross-linking treatment (control); Group II received a proprietary method of cross-linking (see WO2006/066327 incorporated herein by reference); and Group III received the same cross-linking treatment as Group II, but this was followed by the incubating the cross-linked biomaterial with a sterilization solution comprising about 4% v/v propylene oxide and incubating the biomaterial between 30° C. and 55° C. for greater than 48 hours.

Cross-Linking (Fixation) of the Aortic Valve Leaflets

In group I, porcine aortic valve leaflets were cross-linked in a 0.625% glutaraldehyde solution containing 9.07 g/l potassium di-hydrogen phosphate buffer in sterile, deionised water was prepared. The pH of the glutaraldehyde solution was adjusted to 7.4 with sodium hydroxide. The aortic valve leaflets were cross-linked in the glutaraldehyde solution at 1-5° C. for a minimum period of 5 days to crosslink proteins present in the collagen of the tissues.

In group II and III, a water-soluble alcohol-containing solution of 60-80% v/v by volume alcohol ethanol was prepared. The porcine aortic valve leaflets were immersed into the alcohol solution after overnight storage at 4° C. The valved aortic roots were immersed in the same alcohol solution immediately after the final wash in ice-cold 0.9% v/v saline (containing 0.5 mM PMSF). The porcine aortic valve leaflets were kept in the alcohol solution at about 5° C. for a minimum of 24 hours.

The porcine aortic valve leaflets were removed from the alcohol solution and rinsed for about 10 minutes with 0.9% v/v saline. During the rinsing period, the temperature of the rinsing solution was maintained at approximately 10° C.

The aortic valve leaflets were immersed in a 0.625% v/v solution of glutaraldehyde containing 9.07 g/l potassium di-hydrogen phosphate buffer in sterile, deionised water. The pH of the glutaraldehyde solution was adjusted to 7.4 with sodium hydroxide. The pericardium and the valved aortic roots were fixed in the glutaraldehyde solution at 1-5° C. for a minimum period of 24 hours to crosslink proteins present in the collagen of the tissues.

The porcine valve leaflets were removed from the glutaraldehyde solution and rinsed in a sterile 0.9% v/v sodium chloride for about 15 minutes. During the rinsing period, the temperature of the rinsing solution was maintained at approximately 10° C.

The porcine aortic valve leaflets were then immersed in a buffer-free solution containing 8 mg dicarboxylic acid per 1 ml de-ionised water volume. The pH of the solution was adjusted to a pH of 4.5 with a volume of diluted hydrochloric acid. The pericardium and the valved aortic roots were immersed in the solution at a temperature of about 45° C. for about 48 hours.

Final Sterilization and Storage of the Biomaterial

The porcine aortic valve leaflets were then sterilized and stored either by:

(i) immersing the tissue in a 0.25% v/v solution of glutaraldehyde containing 9.07 g/l potassium di-hydrogen phosphate buffer in sterile, deionised water. The pH of the aldehyde solution was adjusted to 7.4 with sodium hydroxide. The process of sterilization was carried out at a temperature about 45° C. for about 120 minutes (Treatment A); or (ii) the porcine aortic valve leaflets were sterilized in an aqueous solution comprising of 4% v/v propylene Oxide by weight combined with 20% v/v ethyl alcohol at 37° C. for about 24 hours and stored in a 4% v/v propylene oxide solution Treatment B—present invention).

Sterilized and stored porcine aortic valve leaflets of all three groups were rinsed in 0.9% v/v saline for 5 minutes. The rinsed tissues were surgically implanted in subcutaneous pockets (one sample of each group per rat), created in the central abdominal wall area of growing (6 weeks old) male Wistar rats. These tissues were removed after 60 days, host tissue removed and samples dried in a Biotherm™ incubator (Selby Scientific, Perth, Wash.) at 90° C. for 48 h. The dried samples were weighed, and the calcium content extracted in 5.0ml 6 N ultrapure hydrochloric acid (Merck, Sydney, Australia) at 75° C. for 24 h. The extractable calcium content was then measured using an atomic absorption spectrophotometer (Varian AA1275) and expressed as µg calcium per mg tissue (dry weight). Results (µg Calcium per mg dried tissue) are summarised in Table 2.

TABLE 2

| Storage solution | Mean ± standard error |
| --- | --- |
| Glutaraldehyde (0.625%) | 174.525 µg Ca/mg Tissue ± 6.884 |
| Treatment A 0.25% Glutaraldehyde | 3.300 µg Ca/mg Tissue ± 0.289 |
| Treatment B 4% propylene Oxide | 1.325 µg Ca/mg Tissue ± 0.317 |

EXAMPLE 4

Effect of Treatment B on Calcification Profile of Bovine Pericardium

In third animal study, the calcification potential of bovine pericardium prepared, cross-linked and stored according to the tissues in Example 3 (0.625% buffered glutaraldehyde, Treatment A+0.2% glutaraldehyde and Treatment B 4% v/v propylene oxide) was compared with the calcification potential of commercial bovine pericardium (Hancock pericardium) stored in a 0.2% glutaraldehyde solution.

Representative samples of each group were trimmed to 1×1 cm size and rinsed in 0.9% v/v saline for 5 minutes.

These samples were surgically implanted in subcutaneous pockets, created in the central dorsal wall area of growing (6 weeks old) male Wistar rats. These tissues were removed after 60 days, host tissue removed and the calcium content determined by atomic absorption spectrophotometry. Results (μg Calcium per mg dried tissue) are summarised in Table 3.

TABLE 3

| Storage solution | Mean ± standard error |
| --- | --- |
| Glutaraldehyde (0.625%) | 136.025 μg Ca/mg Tissue ± 11.385 |
| ADAPT+ 0.25% Glutaraldehyde | 4.100 μg Ca/mg Tissue ± 0.204 |
| ADAPT+ 4% v/v Propylene Oxide | 1.100 μg Ca/mg Tissue ± 0.147 |
| Hancock Pericardium (in 0.2% Glutaraldehyde) | 6.375 μg Ca/mg Tissue ± 1.993 |

EXAMPLE 5

Effect of Treatment B on Calcification Profile of Porcine Aortic Valve Tissue (Valve Leaflets & Aortic Wall) in a Large Animal Model In the fourth animal study, the calcification potential of porcine aortic valve tissue (valve leaflets and aortic wall) prepared, cross-linked in 0.625% buffered glutaraldehyde and stored in (i) 0.625% glutaraldehyde, (ii) treated with Treatment A (0.625% glutaraldehyde) and (iii) treated with Treatment B (4% propylene oxide).

Representative samples of each group were trimmed to an oval shaped size of approximately 1.2×1 cm and rinsed in 0.9% saline for 5 minutes. These samples were surgically implanted in the jugular vein of juvenile sheep (body weight 22-25 kg). These tissues were removed after 150 days, host tissue removed and the calcium content determined by atomic absorption spectrophotometry. Results (μg Calcium per mg dried tissue) are summarised in Table 4-A (Valve leaflets) and Table 4-B (Aortic wall).

TABLE 4-A (Valve leaflets)

| Storage solution | Mean ± standard error |
| --- | --- |
| 0.625% Glutaraldehyde | 211.100 μg Ca/mg Tissue ± 3.134 |
| 2% Propylene Oxide | 93.167 μg Ca/mg Tissue ± 23.764 |
| Treatment B (4% propylene oxide) | 12.775 μg Ca/mg Tissue ± 12.442 |

TABLE 4-B (Aortic wall)

| Storage solution | Mean ± standard error |
| --- | --- |
| 0.625% Glutaraldehyde | 59.444 μg Ca/mg Tissue ± 12.263 |
| 2% Propylene Oxide | 28.633 μg Ca/mg Tissue ± 8.370 |
| Treatment B (4% propylene oxide) | 18.287 μg Ca/mg Tissue ± 7.305 |

EXAMPLE 6

Validation: Sterilisation of Commercial Heart Valve Inoculated With *Bacillus Subtilis* Spores This validation was performed to test the feasibility of sterilising commercial heart valve tissue with 4% propylene oxide after 48 hours at 45° C. The purpose of this feasibility study was to investigate if 3.8% propylene oxide (as a "worst-case" concentration level) is capable of sterilising commercial heart valves X tissue under "worst-case" conditions (contamination with *Bacillus subtilis* spores) prescribed by FDA regulations. The test conditions were:

The valves were removed from the 0.5% Glutaraldehyde and rinsed in a total of 1000 mls of sterile distilled water for a total of 6 mins.

The valve holder and the valve were then aseptically separated and then dried for approximately 30 mins or until visibly dry.

The valve holder and the valve of each device were then inoculated with a total of 20 μl of a suspension of *Bacillus subtilis* spores obtained from STERIS Corporation, USA. The suspension contained $1.25 \times 10^6$ spores.

The valves were then allowed to dry for approximately 1 hour at room temperature.

The devices were then reassembled as per receipt and placed into a sterile jar.

To ten devices, 160 mls of freshly prepared 3.8% propylene oxide was added.

To the final device, 160 mls of Soybean-Casein Digest Medium (SCDM) was added. This was the positive control to assess the viability of the spore suspension. The positive control was incubated at 32° C. for 48 hours.

The ten test valves were then incubated at 42° C. for 44 hours.

Following incubation, a sterility test was performed on each valve.

The valves were separated and each component transferred to an empty sterile jar, to which SCDM was added.

The jars were then incubated at 32° C. for 14 days.

The jars were examined daily for signs of turbidity.

Test details:

Lab Number: 7343042W

Method: Method in Accordance with Test for Sterility, Appendix XVI, British Pharmacopoeia, 2010, and Pharmaceutical Testing Facility Procedure MB:PT:0110.

TABLE 5

| Test | Results |
| --- | --- |
| SCDM: | No growth detected after 14 days incubation at 32° C. |
| Stasis Test: | Performed at expiration of test period. SCDM showed visible growth of *C. albicans* within 48 hours. |
| Positive Control | Growth detected after 24 hours. Growth identified as *B. subtilis*. |

EXAMPLE 7

Effect of Treatment B on Calcification Profile of Commercial Heart Valve Tissue (Bovine Pericardial Tissue) in a Small Animal Model Table 6 shows the results of a fifth animal study in which the calcification potential of bovine pericardium cross-linked and sterilised in 0.625% v/v glutaraldehyde (which served as a reference control—marked A) was compared with commercial heart valve tissue (bovine pericardium, cross-linked and stored according to a commercial proprietary protocol which is 0.625% v/v buffered glutaraldehyde cross-linking+formaldehyde storage—marked B) and the same commercial heart valve tissue sterilised at 45° C. for 48 hours in 4% v/v propylene oxide and stored in 4% v/v propylene oxide solution—marked C.

Representative samples of each group were trimmed to 1×1 cm size and rinsed in 0.9% v/v saline for 5 minutes. These samples were surgically implanted in subcutaneous pockets, created in the central dorsal wall area of growing (6 weeks old) male Wistar rats. These tissues were removed after 8, 16 and 24 weeks, host tissue removed and the calcium content determined by atomic absorption spectrophotometry. Results (μg Calcium per mg dried tissue) are summarised in Table 6.

TABLE 6

| | Storage solutions | | |
|---|---|---|---|
| | A | B | C (Present Invention) |
| 8 Weeks | 85 μg Ca/mg Tissue ± 12 | 12 μg Ca/mg Tissue ± 11 | 0.751 μg Ca/mg Tissue ± 0.2 |
| 16 Weeks | 94 μg Ca/mg Tissue ± 12 | 10 μg Ca/mg Tissue ± 8 | 0.74 μg Ca/mg Tissue ± 0.2 |
| 24 Weeks | 134 μg Ca/mg Tissue ± 12 | 8 μg Ca/mg Tissue ± 6 | 3.56 μg Ca/mg Tissue ± 3 |

EXAMPLE 8

Effect of Treatment B on Calcification Profile of Commercial Heart Valve Tissue (Bovine Pericardial) Tissue in a Rapid In Vitro Calcification Model In a further experimental assessment, the calcification potential of commercial valve tissue (control tissue) was compared with commercial heart valve tissue sterilised at 45° C. for 48 hours in 4% propylene oxide and stored in 4% propylene oxide solution (treated tissue) in a rapid in vitro calcification model.

Stented commercial heart valves (control and treated) were mounted in a Rowan Ash Fatigue tester and exposed to a physiological solution (with a high calcium/phosphate content) during accelerated flow (400 test cycles per minute) up to 50 million cycles.

After 50 million test cycles, heart valves were removed and a represented tissue sample taken for histology. The remaining tissue of each of the three valve leaflets in each valve were removed and the calcium content determined by atomic absorption spectrophotometry. Results (μg Calcium per mg dried tissue) are summarised in Table 7.

TABLE 7

| Valve tissue | Mean ± standard error |
|---|---|
| Commercial valve | 49.71 μg Ca/mg tissue ± 2.112 |
| Commercial valve + 4% Propylene Oxide | 32.34 μg Ca/mg tissue ± 1.336 |

EXAMPLE 9

Figure 2:
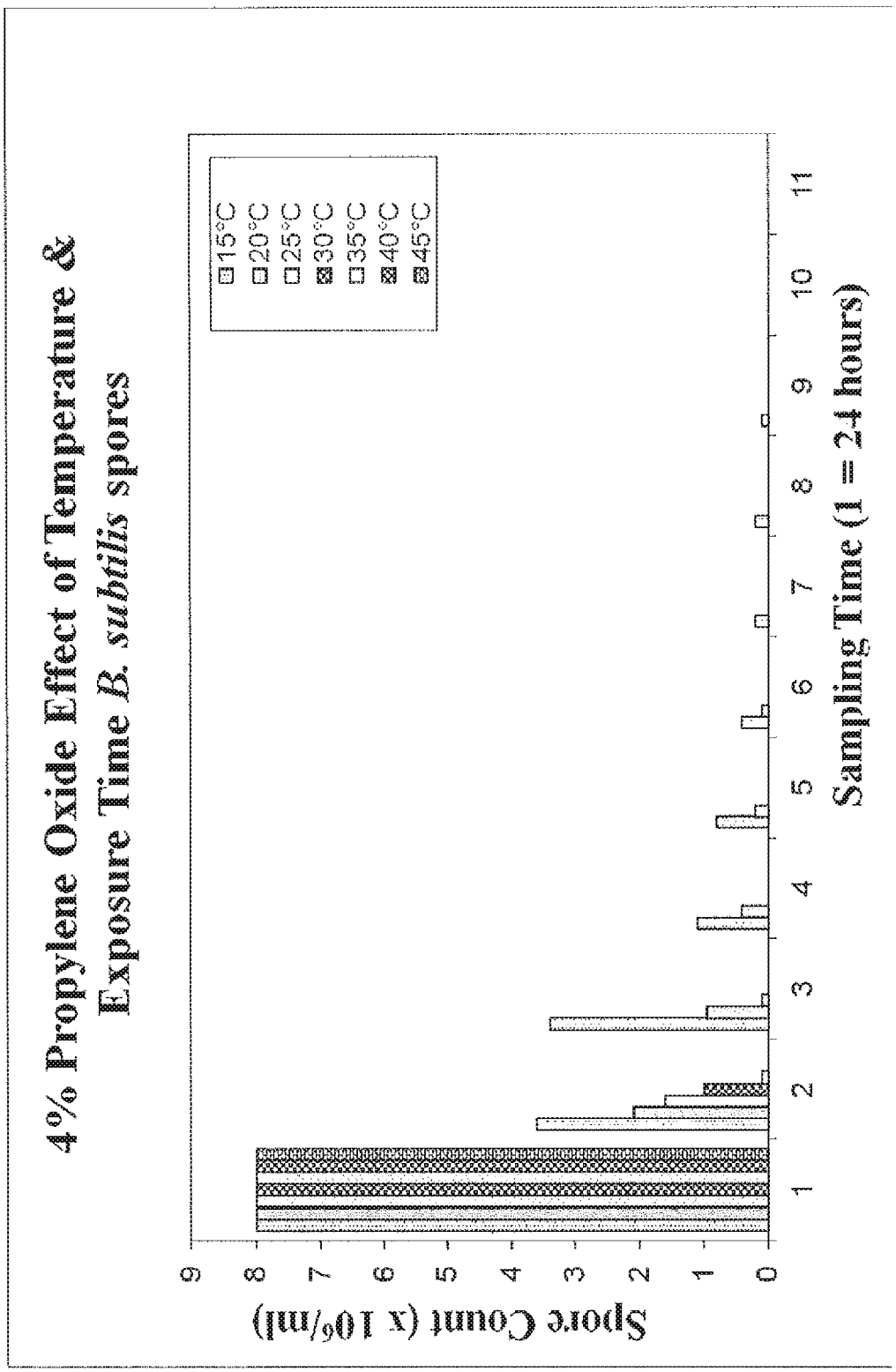
FIG. 2 shows the effect of 4% propylene oxide at varying temperatures between 15° C. and 45° C. on *B. subtilis* spores over time.

Effect of Sterilization and Storage Methodology Tissue Inoculated with *Bacillus subtilis* Spores FIGS. 1 and 2 show the effect of 2% v/v and 4% v/v propylene oxide (respectively) at varying temperatures between 15° C. and 45° C. on *B. subtilis* spores over time. The experiment conditions used are described in Example 6. Essentially, it can be seen the neither sterilization solutions (2% or 4%) has little sterilization effect before 48 hours. It can also be seen from FIG. 2 that within 48 hours the effect of increasing temperature has a profound effect on sterilization. For example, at a temperature of 40° C. and above there was sterilization after 24 hours and that by 48 hours there was sterilization even at temperatures of 25° C. and above. FIG. 1 shows that in order to obtain sterilization with 2% v/v propylene oxide the tissue needs to be incubated for at least 6 days at temperatures above 35° C. Even incubation for 10 days at 15 to 20° C. has no material effect on sterilization with 2% v/v propylene oxide.

Thus, it can be seen from FIGS. 1 and 2 that optimal sterilization is obtained by incubating the tissue with a 4% v/v propylene oxide solution and incubating the tissue at about 45° C. for greater than 48 hours.

The claims defining the invention are as follows:

1. A containerized, sterilized cross-linked collagen-based biomaterial comprising:
   (i) a sterile closed, storage container;
   (ii) a sterilized, cross-linked collagen-based biomaterial disposed within the closed, storage container for both sterilization and storage of the cross-linked collagen-based biomaterial;
   (iii) a storage solution comprising 3% to 6% v/v propylene glycol disposed within the closed, storage container;
   wherein the storage solution results from in situ conversion of a 3% to 6% v/v propylene oxide sterilization solution in the closed, storage container in the presence of the cross-linked collagen-based biomaterial at an incubation temperature between about 30° C. and 55° C. for greater than 48 hours, wherein the sterilization solution does not include alcohol.

2. The containerized, sterilized cross-linked collagen-based biomaterial of claim 1, wherein the incubation temperature is at 45° C. for greater than 48 hours.

3. The containerized, sterilized cross-linked collagen-based biomaterial of claim 1, wherein the incubation temperature is reduced to room temperature after said 48 hours.

4. The containerized, sterilized cross-linked collagen-based biomaterial of claim 1, wherein the storage solution in (iii) comprises between 3.8% and 4.5% v/v propylene glycol.

5. The containerized, sterilized, cross-linked collagen-based material of claim 1, wherein the storage solution in (iii) comprises 4% v/v propylene glycol.

6. The containerized, sterilized cross-linked collagen-based biomaterial of claim 1, wherein the cross-linked collagen-based biomaterial comprises collagen-containing tissue isolated from an ovine, a bovine, a caprine, an equine, a porcine, a marsupial or a human.

7. The containerized, sterilized cross-linked collagen-based biomaterial of claim 1, wherein the cross-linked collagen-based biomaterial comprises cellular tissue selected from the group consisting of cardiovascular tissue, heart tissue, heart valve, aortic roots, aortic wall, aortic leaflets, pericardial tissue, connective tissue, dura mata, dermal tissue, a vascular tissue, cartilage, pericardium, ligament, tendon, blood vessels, umbilical tissue, bone tissue, fasciae, and submucosal tissue and skin.

8. The containerized, sterilized cross-linked collagen-based biomaterial of claim 1, wherein the cross-linked collagen-based biomaterial further comprises synthetic analogs formed from synthetic polymers, biological polymers, or both.

9. A method for sterilizing and storing a cross-linked collagen-based biomaterial comprising:
(i) contacting said cross-linked collagen-based biomaterial with a solution in a container to sterilize the cross-linked collagen-based biomaterial, the solution comprising between 3% and 6% v/v propylene oxide and incubating said cross-linked collagen-based biomaterial at an incubation temperature between about 30° C. and 55° C. for greater than 48 hours, wherein the solution does not include alcohol; and then
(ii) storing said cross-linked collagen-based biomaterial in the solution in the same container for at least 4 days or until the propylene oxide has converted in situ to propylene glycol in the presence of the cross-linked collagen-based biomaterial.

10. The method of claim 9, wherein the incubation temperature is about 45° C.

11. The method of claim 9, wherein the incubation temperature is allowed to reduce to room temperature after said 48 hours.

12. The method of claim 9, wherein sterilizing solution comprises between 3.8% and 4.5% v/v propylene oxide.

13. The method of claim 9, wherein the sterilizing solution comprises 4% v/v propylene glycol.

14. A method of sterilizing and storing cross-linked collagen-based biomaterial in a single container, the method comprising:
(i) disposing an initially unsterilized cross-linked collagen-based biomaterial into a sterilization solution within the container, the container to be used for both sterilization of the cross-linked collagen-based biomaterial and storage of the cross-linked collagen-based biomaterial, wherein the sterilization solution is a 3% to 6% v/v propylene oxide solution;
(ii) sterilizing the cross-linked collagen-based biomaterial with the sterilization solution by incubating the container at an incubation temperature between about 30° C. and 55° C. for an incubation period of at least 48 hours;
(iii) storing the cross-linked collagen-based biomaterial in the same container as the sterilization step, wherein the sterilization solution has converted in situ in the presence of the cross-linked collagen-based biomaterial into a storage solution of 3% to 6% v/v propylene glycol, and wherein the sterilization solution does not include alcohol.

15. The method of claim 14, wherein the incubation temperature is 45° C.

16. The method of claim 15, wherein a temperature of the container is allowed to reduce to room temperature after said incubation period.

17. The method of claim 14, wherein the storage solution in step (iii) comprises between 3.8% and 4.5% v/v propylene glycol.

18. The method of claim 14, wherein the storage solution in step (iii) comprises 4% v/v propylene glycol.

* * * * *